United States Patent
Yokoyama et al.

(10) Patent No.: US 7,598,233 B2
(45) Date of Patent: Oct. 6, 2009

(54) METHOD FOR TREATING THROMBOSIS

(75) Inventors: Toru Yokoyama, Tokyo (JP); Taro Aoki, Tokorozawa (JP)

(73) Assignees: Kowa Co., Ltd., Nagoya-shi (JP); Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 11/158,080

(22) Filed: Jun. 22, 2005

(65) Prior Publication Data

US 2006/0217352 A1    Sep. 28, 2006

Related U.S. Application Data

(60) Provisional application No. 60/665,390, filed on Mar. 28, 2005.

(51) Int. Cl.
*A61K 31/60* (2006.01)
*A61K 31/44* (2006.01)
*A01N 37/36* (2006.01)
*A01N 43/42* (2006.01)

(52) U.S. Cl. ...................................... 514/165; 514/299

(58) Field of Classification Search .................. 514/165, 514/299
See application file for complete search history.

(56) References Cited

U.S. PATENT DOCUMENTS

| 5,856,336 A | 1/1999 | Fujikawa et al. |
| 6,235,706 B1 * | 5/2001 | Gould et al. .................... 514/2 |
| 6,465,477 B1 | 10/2002 | Muramatsu et al. |
| 2003/0114685 A1 * | 6/2003 | Niddam-Hildesheim et al. .......................... 548/530 |

OTHER PUBLICATIONS

Markle et al. "Pitavastatin Alters the Expression of Thrombotic and Fibrinolytic Proteins and Human Vascular Cells". Journal of Cellular Biochemistry, 2003; 90:23-32.*
"Structure-Activity Relationship and Drug Design". Remington's Pharmaceutical Sciences (Sixteenth Edition). Mack Publishing, 1980. pp. 420-425.*
Taylor Jr. "Chapter 3: Propagation of Uncertainties". An Introduction to Error Analysis: The Study of Uncertainties in Physical Measurements (Second Edition). University Science Books, 1997. pp. 45-79.*

* cited by examiner

*Primary Examiner*—Ardin Marschel
*Assistant Examiner*—Leslie A Royds
(74) *Attorney, Agent, or Firm*—Oblon, Spivak, McClelland, Maier & Neustadt, L.L.P.

(57) ABSTRACT

This invention relates to a method for treating thrombosis by combined administration of a pitavastatin with aspirin.

18 Claims, 1 Drawing Sheet

METHOD FOR TREATING THROMBOSIS

TECHNICAL FIELD

This invention relates to a method for treating thrombosis, and more specifically, to a method for treating thrombosis which is effective for both suppressing blood coagulation and promoting thrombolysis.

BACKGROUND ART

In the case of thrombosis, blood circulation failure is caused by the thrombus formed in the inside of an artery or a vein by one or more of platelet hyperaggregation, hypercoagulability by activation of the blood coagulation factor, and reduced thrombolytic ability. The resulting ischemia leads to reduction of oxygen and nutrients in the peripheral tissues including brain, heart, and other organs, and this mechanism is strongly related to the onset of diseases such as cerebral infarction and myocardial infarction which may result in fatal symptoms. Therefore, treatment of thrombosis is viewed as an important remedy in these diseases.

Various drugs are currently used for the treatment of thrombosis. Exemplary such drugs include antiplatelets which suppress platelet aggregation such as aspirin, ticlopidine, eicosapentaenoic acid (EPA), dipyridamole, and dilazep hydrochloride, and anticoagulants which suppress blood coagulation factor such as warfarin, heparin, low molecular weight heparin, and argatroban. These drugs are used either alone of in combination of two or more.

An antiplatelets such as aspirin suppresses formation of thrombus and clot at the impaired site of the blood vessel by suppressing development of the blood coagulation triggered by platelet aggregation by suppressing the formation of the aggregants. However, since platelets also bear the function of preventing hemorrhage from the blood vessel, excessive suppression of the platelet invites loss of physiological prevention of hemorrhage, and antiplatelet administration of the level sufficient for treating the thrombosis often causes difficulties.

In addition, since an antiplatelet such as aspirin does not exhibit direct anticoagulant action, it is often difficult to realize sufficient antithrombotic action solely by the antiplatelet in the patient suffering from the thrombosis.

Aspirin is also known to cause aspirin dilemma when it is administered at a high dose. More specifically, aspirin is known to induce a serious gastrointestinal dysfunction since physiological production of the substance protecting gastrointestinal mucosa is suppressed, and also, a dysfunction of blood circulation system since physiological production of vasodilator is suppressed. Accordingly, an escalation of the aspirin dose is not recommended. Administration of aspirin at a dose sufficient for the thrombosis treatment is also difficult in this respect.

In the meanwhile, administration of the anticoagulant at high dose is associated with the risk of side effects, and administration of the anticoagulant at a dose sufficient for the thrombosis treatment is also difficult.

Accordingly, combined administration of an antiplatelet such as aspirin at an adequate dose and an anticoagulant at an adequate dose is often useful in treating the thrombosis.

However, prevention of the thrombus formation is accomplished by an antiplatelet and an anticoagulant by different mechanisms, and bleeding tendency may become enhanced at a certain dose.

A new drug for treating thrombosis is disclosed in WO98/11896, wherein an antithrombotic comprising a combination of HMG-CoA reductase inhibitor and aspirin is administered. HMG-CoA reductase inhibitor, which is known for its strong inhibitory action for HMG-CoA reductase, is used for reducing blood cholesterol. This drug, however, is not conceived as a therapeutic drug of thrombosis. In addition, WO98/11896 does not specifically describe effects that would be achieved if HMG-CoA reductase inhibitor is administered by a combined administration, and the extent of the therapeutic effect remains unknown. Furthermore, there is no indication for the effects that would be achieved by the combined administration of a pitavastatin (U.S. Pat. No. 5,856,336, and Japanese Patent Application Laid Open No. 1-279866) which is a HMG-CoA reductase inhibitor with aspirin.

SUMMARY OF THE INVENTION

Accordingly, an object of the present invention is to provide a method for treating thrombosis which is effective in both suppressing the blood coagulation and promoting the thrombolysis, without causing severe side effects.

In view of the situation as described above, the inventors of the present invention made an intensive study and found that a combined administration of a pivastatin and aspirin will result in an enhanced suppression of the blood coagulation as well as improved promotion of the thrombolysis which are effective for treating thrombosis. The present invention is based on such a finding.

Accordingly, the present invention provides a method for treating thrombosis by combined administration of a pitavastatin with aspirin.

The method for treating thrombosis of the present invention exhibits excellent antithrombotic action in terms of both improved anticoagulant action and enhanced promotion of thrombolysis, and therefore, this method is useful in treating thrombosis associated with hypertension, vasospasm, arteriosclerosis, diabetes, surgery, blood congestion, or the like which has occurred either alone or in combination of two or more. The combined administration of a pitavastatin and aspirin also exhibits stronger antithrombotic action than sole administration of the aspirin, and therefore, such combined administration can avoid high dose aspirin administration associated with the side effects as well as the side effects of the aspirin itself since the dose of aspirin can be reduced.

BEST MODE FOR CARRYING OUT THE INVENTION

Figure 1:
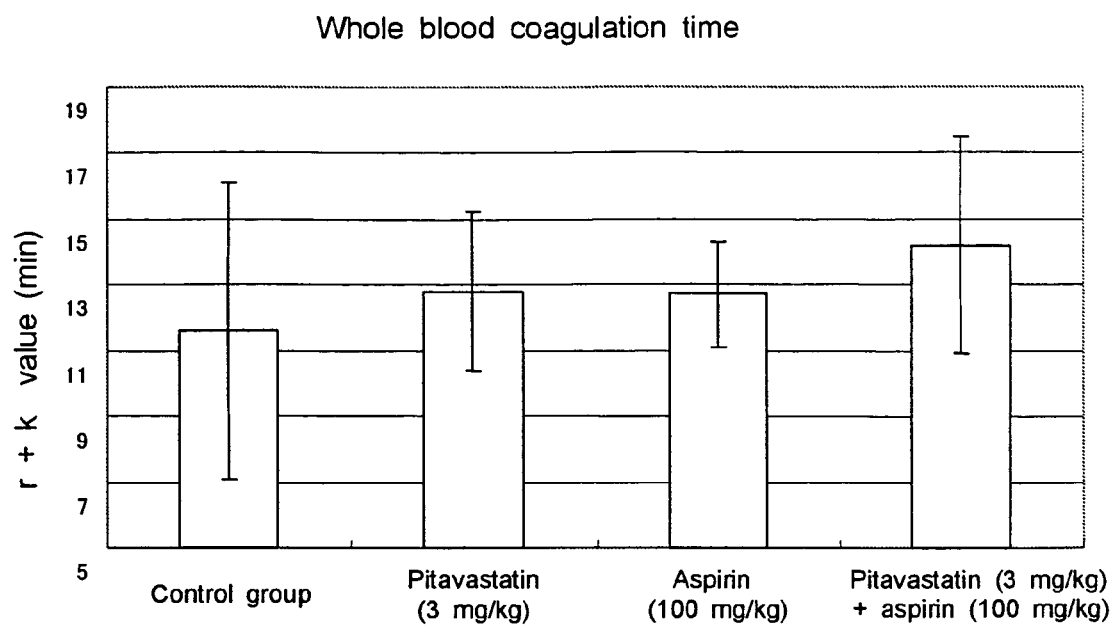
FIG. 1 is a view showing the effects of the combined administration of aspirin and pivastatin calcium (indicated as pivastatin) in elongating thromboelastograph whole blood coagulation time (r+k value) (in increasing anticoagulant action).

The pitavastatins used in the present invention include pitavastatin (3R,5S,6E)-7-[2-cyclopropyl-4-(4-fluorophenyl)-3-quinolyl]-3,5-dihydroxy-6-heptenoic acid (U.S. Pat. No. 5,856,336 and Japanese Patent Application Laid Open No. 1-279866), pitavastatin forming a lactone ring, its salt, its hydrate, and a solvate thereof with a pharmaceutically acceptable solvent. Exemplary salts include alkaline metal salts such as sodium salt and potassium salt; alkaline earth metal salts such as calcium salt and magnesium salt; and organic amino salt or ammonium salt such as phenylethylamine salt. Among these, the pitavastatin is preferably a pitavastatin salt, and in particular calcium salt.

The pitavastatins can be produced by the method described in U.S. Pat. No. 5,856,336 or Japanese Patent Application Laid Open No. 1-279866.

The aspirin used in the invention is acetyl salitylic acid and it is readily available as a commercial product. Alternatively, the aspirin may be in the form of a salt with sodium, calcium, or aluminum.

The method for treating thrombosis of the present invention is a combined administration of a pitavastatin and aspirin, and as will be described in the Examples below, such combined administration of the pitavastatin and the aspirin to a guinea pig exhibited elongated blood coagulation time (an enhanced anticoagulant action) as well as an increased suppression of the maximal clot formation (enhanced thrombolysis) compared to the sole administration of the pitavastatin or the aspirin.

Therefore, the method for treating thrombosis of the present invention is useful in treating thrombosis occurring as a result of blood vessel disorder associated with hypertension, vasospasm, arteriosclerosis, diabetes, surgery, blood congestion, and other diseases occurring solely or as a combination.

In the method for treating thrombosis of the present invention, an administration mode of the pitavastatin and the aspirin is not particularly limited, and the pitavastatin and the aspirin may be administered either separately or in a single preparation, and either simultaneously or in separate preparation at a certain interval. The pitavastatin and the aspirin may also be administered in different frequency.

When the pitavastatin and the aspirin are administered in a single preparation, they may be combined at a mass ratio in the range of 1:2.5 to 1:300, more preferably, at 1:2.5 to 1:150.

The pitavastatin and the aspirin may be mixed with a pharmaceutically acceptable diluent, excipient, or the like to prepare single preparation. Alternatively, the pitavastatin and the aspirin may be separately prepared to produce a set (kit) comprising these preparations. When they are administered separately, they do not have to be in the same dosage form.

The drugs of the present invention may be administered orally, for example, in the form of tablet, capsule, granule, powder, solution, or syrup.

In addition to the effective components, the preparation may include a suitable pharmaceutically acceptable excipient, disintegrant, binder, lubricant, diluent, buffer, isoelectric agent, antiseptic, lubricant, emulsifier, dispersant, stabilizer, solubilizer, or the like according to its dosage form. The preparation may be produced by mixing, diluting, or dissolving the effective components with such additive, and the preparation may be accomplished by any method commonly used in the art.

In the present invention, the dose of the pitavastatin and the aspirin may be appropriately selected according to the body weight, age, sex, symptom, and the like of the patient. In the case of an adult, typical daily dose of the pitavastatin is 1 to 100 mg, preferably 1 to 50 mg, more preferably 1 to 20 mg, and typical daily dose of the aspirin is 10 to 300 mg, preferably 10 to 100 mg, which may be administered at a single dose or in two or more divided doses.

EXAMPLES

Next, the present invention is described in further detail by referring to the Examples which by no means limit the scope of the present invention.

Example 1

Effects of Combined Administration of Aspirin and Pivastatin Calcium on Whole Blood Coagulation Time (r+k Value) (Anticoagulant Action)and Maximal Amplitude (MA) of Clot Formation (Promotion of Thrombolysis)

Effects of the administration of aspirin and pitavastatin calcium on whole blood coagulation time (r+k value) and maximal amplitude (MA) of clot formation were evaluated as described below in (1) to (4), and the results are shown in (5) (r, reaction time; k, clotting time; MA, Maximal Amplitude).

(1) Test Animal and Breeding Conditions

The animals used in the test were 6 week old Hartley male guinea pigs (Japan SLC, Inc.), and these animals were kept throughout the test period in a breeding chamber with controlled day and night cycle (light period under illumination of room light, 7 am to 7 pm) at a temperature of 23±3° C. and a humidity of 55±15%. The animals were fed pellets (RC4; Oriental Yeast Co., Ltd.) and tap water ad libitum.

(2) Preparation of the Drug

Pitavastatin calcium and aspirin were respectively suspended in 0.5 mass% aqueous solution of sodium carboxymethylcellulose (Product of Iwai Chemicals Company) to a concentration of 1 mg/mL and 10 mg/mL. In the case of pitavastatin calcium which contains 9.43 mass% of water, the dose was corrected by weighing 1.1 folds of the dose. The suspension was stored in a dark bottle and refrigerated at 4° C., and the suspension was renewed every 7 days.

(3) Test Procedure 24 guinea pigs were divided into 4 groups (5 or 6 animals in each group), namely, control group (with no drug administration), the group solely administered with pitavastatin calcium (3 mg/kg), the group solely administered with aspirin (100 mg/kg), and the group administered with a combination of pitavastatin calcium (3 mg/kg) and aspirin (100 mg/kg). Both drugs were orally administered once a day (at 4 pm) for 14 days, and the control group was orally administered with 1 mL/kg of 0.5 mass% aqueous solution of sodium carboxymethylcellulose. Blood was collected from the animals of all groups after 18 hours of fasting from the final administration, and the whole blood coagulation time (r+k value) and the maximal amplitude (MA) of clot formation were measured using Thromboelastograph (Product of Helige).

(4) Data Processing

The results are all shown in average ± standard deviation.

(5) Test Results

As shown in FIG. 1 and Table 1 (wherein pitavastatin calcium is indicated as pitavastatin), some elongation in the whole blood coagulation time (r+k value) was observed in the groups receiving the sole administration of pitavastatin calcium or aspirin (110% and 109%). In contrast, the group receiving the combined administration of pitavastatin calcium and aspirin exhibited a remarkable elongation in the whole blood coagulation time (122%) compared to the groups of sole administration, and the effects were synergistic (Bürge equation).

More specifically, the effect of the combined administration was larger than the product of the effects of the sole administrations (122%>110%×109%=120%).

Figure 2:
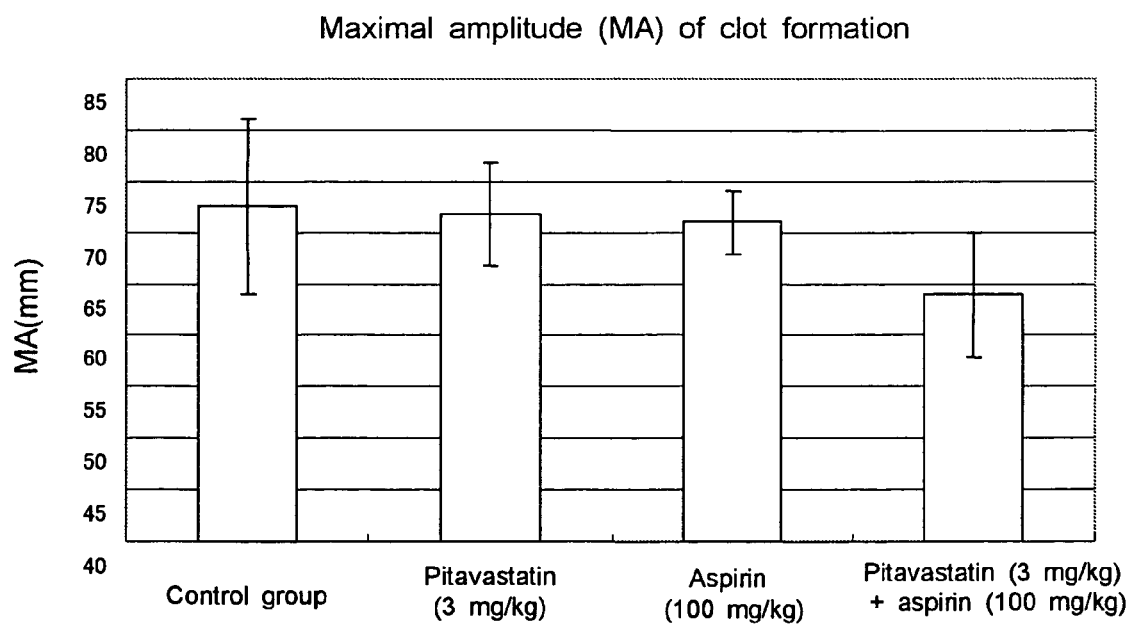
FIG. 2 is a view showing the effects of the combined administration of aspirin and pivastatin calcium (indicated as pivastatin) in suppressing maximal amplitude (MA) of clot formation (in promoting fibrinolytic action).

In addition, as shown in FIG. 2 and Table 2 (wherein pitavastatin calcium is indicated as pitavastatin), while some suppression in maximal amplitude (MA) of clot formation was observed in the groups receiving the sole administration of pitavastatin calcium or aspirin (99% and 98%), the group receiving the combined administration of pitavastatin calcium and aspirin exhibited remarkably suppressed maximum clot amplitude (88%) compared to the groups of sole administration, and the effects were synergistic (Bürge equation).

More specifically, the effect of the combined administration was larger than the product of the effects of the sole administrations (88%<99%×98%=97%).

As demonstrated above, the combined administration of the aspirin and the pitavastatin was confirmed to exhibit very strong antithrombotic action in terms of both suppressing the blood coagulation and promoting the thrombolysis compared to the sole administration of the aspirin or the pitavastatin.

TABLE 1

| Dose | | Case number | Whole blood coagulation time (r + k value), min | Relative value (%) |
| --- | --- | --- | --- | --- |
| Pitavastatin | Aspirin | | | |
| 0 mg/kg | 0 mg/kg | 6 | 11.6 ± 4.5 | 100 |
| 3 mg/kg | 0 mg/kg | 6 | 12.8 ± 2.4 | 110 |
| 0 mg/kg | 100 mg/kg | 6 | 12.7 ± 1.6 | 109 |
| 3 mg/kg | 100 mg/kg | 5 | 14.2 ± 3.3* | 122 |

(The results are all shown in average ± standard deviation; *synergistic effect)

TABLE 2

| Dose | | Case number | Maximal amplitude (MA) of clot formation, mm | Relative value, % |
| --- | --- | --- | --- | --- |
| Pitavastatin | Aspirin | | | |
| 0 mg/kg | 0 mg/kg | 6 | 72.5 ± 8.6 | 100 |
| 3 mg/kg | 0 mg/kg | 6 | 71.8 ± 5.0 | 99 |
| 0 mg/kg | 100 mg/kg | 6 | 71.0 ± 3.1 | 98 |
| 3 mg/kg | 100 mg/kg | 5 | 63.9 ± 6.0* | 88 |

(The results are all shown in average ± standard deviation; *synergistic effect)

Comparative Example

Effects of Combined Administration of Aspirin and Atorvastatin Calcium Hydrate on Whole Blood Coagulation Time (r+k Value) and Maximal Amplitude (MA) of Clot Formation Effects of the drug administration on the whole blood coagulation time (r+k value) and the maximal amplitude (MA) of clot formation were determined by repeating the procedure of Example 1 except for the use of atorvastatin calcium hydrate which is a typical HMG reductase inhibitor (U.S. Pat. Nos. 4,681,893 and 5,273,995; and Japanese Patent Application Laid Open No. 3-58967) instead of the pitavastatin calcium. Atorvastatin calcium hydrate was administered at a dose of 15 mg/kg.

The group receiving the combined administration of atorvastatin calcium hydrate and aspirin did not exhibit elongation in the whole blood coagulation time (r+k value). This group also failed to exhibit suppression of the maximal amplitude (MA) of clot formation.

Thus, neither suppression of the blood coagulation nor promotion of the thrombolysis were confirmed in the combined administration of atorvastatin calcium hydrate and aspirin.

As described above, neither elongation of the whole blood coagulation time nor suppression of the maximum clot amplitude were observed in the combined administration of atorvastatin calcium hydrate and aspirin while synergy of these effects were observed in the combined administration of pitavastatin calcium and aspirin. The utility of the combined administration of the present invention were thus confirmed.

The invention claimed is:

1. A method for treating thrombosis comprising:
   administering to a subject in need thereof an amount of pitavastatin, or a salt or solvate thereof, and an amount of aspirin, said amounts being effective to treat thrombosis, wherein pitavastatin and aspirin are administered in a single preparation at a mass ratio of 1:2.5 to 1:150.

2. The method of claim 1, wherein a salt of pitavastatin is administered.

3. The method of claim 1, wherein pitavastatin calcium is administered.

4. The method of claim 1, wherein a pitavastatin solvate is administered.

5. The method of claim 1, comprising administering to an adult human a daily dose of pitavastatin ranging from 1 to 50 mg and a daily dose of aspirin ranging from 10 to 100 mg.

6. The method of claim 1, wherein the thrombosis is associated with hypertension.

7. The method of claim 1, wherein the thrombosis is associated with vasospasm.

8. The method of claim 1, wherein the thrombosis is associated with arteriosclerosis.

9. The method of claim 1, wherein the thrombosis is associated with diabetes.

10. The method of claim 1, wherein the thrombosis is associated with surgery.

11. The method of claim 1, wherein the thrombosis is associated with blood congestion.

12. The method of claim 1, wherein aspirin is administered in a daily dose of 100 to 300 mg.

13. The method of claim 1, wherein aspirin is administered in a daily dose of 10 to 100 mg.

14. The method of claim 1, wherein pitavastatin and aspirin are administered in a mass ratio of 1:3 to 1:100.

15. A method for treating thrombosis comprising:
    administering to a subject in need thereof an amount of pitavastatin or a salt or solvate thereof, and an amount of aspirin, said amounts being effective to treat thrombosis and to provide synergistic antithrombotic actions compared to administration of pitavastatin or aspirin alone.

16. The method of claim 15, wherein pitavastatin is administered at a daily dose ranging from 1 to 100 mg and aspirin is administered in a daily dose ranging from 10 to 300 mg.

17. A method for treating thrombosis comprising:
    administering daily 1-50 mg of pitavastatin, or a salt or solvate thereof, and 10-100 mg of aspirin to a subject in need thereof; wherein the pitavastatin and aspirin are administered separately.

18. The method of claim 1, wherein pitavastatin and aspirin are administered in a mass ratio of 1:5 to 1:100.

* * * * *